US006580268B2

(12) United States Patent
Wolodko

(10) Patent No.: US 6,580,268 B2
(45) Date of Patent: Jun. 17, 2003

(54) SUCKER ROD DIMENSION MEASUREMENT AND FLAW DETECTION SYSTEM

(75) Inventor: Ben B. Wolodko, Edmonton (CA)

(73) Assignee: Weatherford/Lamb, Inc., Houston, TX (US)

( * ) Notice: Subject to any disclaimer, the term of this patent is extended or adjusted under 35 U.S.C. 154(b) by 0 days.

(21) Appl. No.: 09/940,865

(22) Filed: Aug. 28, 2001

(65) Prior Publication Data

US 2003/0042897 A1 Mar. 6, 2003

(51) Int. Cl.$^7$ ............................. G01V 3/10; G01V 3/18
(52) U.S. Cl. .................... 324/240; 324/239; 324/227
(58) Field of Search .......................... 324/240, 238, 324/239, 228, 262, 241, 242, 227

(56) References Cited

U.S. PATENT DOCUMENTS

| 2,855,564 | A |   | 10/1958 | Irwin et al. ............... 324/37 |
| 4,492,115 | A |   | 1/1985  | Kahil et al. .............. 73/151 |
| 4,636,727 | A | * | 1/1987  | Kahil et al. .............. 324/240 |
| 5,793,205 | A | * | 8/1998  | Griffith et al. ............ 324/238 |

FOREIGN PATENT DOCUMENTS

| CA | 2166953     | 7/1996 | ........... G01R/33/12 |
| EP | 0 845 672 A1 | 6/1998 | ........... G01N/27/82 |
| WO | WO 98/16842 | 4/1998 | ........... G01R/33/12 |

OTHER PUBLICATIONS

Herbert R. Weischedel, "The Inspection of Wire Ropes in Service: A Critical Review".
PCT International Search Report, International Application No. PCT/GB 02/03835, dated Nov. 8, 2002.
Mark GJ Beretta, "How Magnetic Testing is Being Used to Examine Wire Rope Interior," *Offshore*, Sep. 2001, pp. 110 and 111.

* cited by examiner

*Primary Examiner*—Edward Lefkowitz
*Assistant Examiner*—Subhash Zaveri
(74) *Attorney, Agent, or Firm*—Moser, Patterson & Sheridan, L.L.P.

(57) ABSTRACT

Apparatus and methods for measuring cross sectional area and flaws in a continuous sucker rod string as the string is conveyed within a borehole. These measured parameters are useful is monitoring the physical integrity of the sucker rod string. A magnet is used to saturate an increment of continuous sucker rod, and a coil is used to measure induced flux. Cross sectional area of the rod increment is computed from the flux measurement. One or more Hall effect transducers are used to measure leakage from the increment as a function of distance along the increment. This measurement is used to detect and quantify the type of flaw within the rod increment being investigated. The process is repeated as the sucker rod string is conveyed into or out of the borehole.

20 Claims, 2 Drawing Sheets

SUCKER ROD DIMENSION MEASUREMENT AND FLAW DETECTION SYSTEM

BACKGROUND OF THE INVENTION

1. Field of the Invention

This invention is directed toward artificial lift systems used to produce fluids from boreholes such as oil and gas wells. More particularly, the invention is directed toward apparatus and methods for measuring dimensions and flaws in coiled sucker rod as the rod string is removed from or inserted into the borehole.

2. Background of the Art

Oil and gas wells are typically drilled with a rotary drill bit and a circulating drilling fluid or "mud" system. Subsequent to the drilling of a well, or alternately at intermediate periods during the drilling process, the borehole is cased typically with steel casing, and the annulus between the borehole and the outer surface of the casing is filled with cement. The casing preserves the integrity of the borehole by preventing collapse or cave-in. The cement annulus hydraulically isolates formation zones penetrated by the borehole that are at different internal formation pressures. Producing zones are typically produced through tubing suspended within the casing.

Fluids can be produced from oil and gas wells by utilizing internal pressure within a producing zone to lift the fluid through the well borehole to the surface of the earth. If internal formation pressure is insufficient, artificial fluid lift means and methods must be used to transfer fluids from the producing zone and through the borehole to the surface of the earth.

The most common artificial lift technology utilized in the domestic oil industry is the sucker rod pumping system. A sucker rod pumping system consists of a pumping unit that converts a rotary motion of a drive motor to a reciprocating motion of an artificial lift pump. A pump unit is connected to a polish rod and a sucker rod "string" which, in turn, operationally connects to a rod pump in the borehole. The string can consist of a group of connected, essentially rigid, steel sucker rods sections (commonly referred to as "joints") in lengths of 25 or 30 feet (ft), and in diameters ranging from ⅝ inches (in.) to 1¼ in. Joints are sequentially connected or disconnected as the string is inserted or removed from the borehole, respectively. Alternately, a continuous sucker rod in diameters ranging from ¾ inches (in.) to 1¼ in. (hereafter referred to as COROD) string can be used to operationally connect the pump unit at the surface of the earth to the rod pump positioned within the borehole. A delivery mechanism rig (hereafter CORIG or any injector) is used to convey the COROD string into and out of the borehole.

A prior art borehole pump assembly of a sucker rod operated artificial lift systems typically utilizes a progressing cavity pump (hereafter PCP) positioned within wellbore tubing. The PCP consists of a rotor operating within a stator, and is positioned at or near a formation to be produced. The sucker rod string is rotated from surface of the earth by a rotary well head drive, thereby imparting rotation to the rotor element of the PCP to provide desired fluid lifting. This system has proven to be an effective means of lifting primary heavy oil formations where sand is suspended within the produced fluid. As the sand laden oil mixture rises in the tubing string, the fluid acts like abrasive slurry that abrades the sucker rod string. This abrasion can be general over a length of the rod thereby altering the cross section area of the rod string over an extended length. Abrasion can be localized to form a groove or a ring around a limited vertical extent of the sucker rod string. Significant abrasive wear can lead to mechanical failure of the rod. In addition, produced fluids are often corrosive. These corrosive fluids can attack the sucker rod surface causing pitting that may lead to fatigue cracking and subsequent rod failure.

To summarize, fluids produced with a PCP operated with a COROD sucker rod system can adversely alter the sucker rod string. The fluid can abrade the sucker rod string over an extended length thereby reducing cross sectional area of the string. The fluid can "incise" groves or rings in vertically localized sections of the rod string thereby forming localized flaws. Corrosive fluid can pit or otherwise distort virtually any portion of the rod string that it contacts. All of these alterations can adversely affect the physical integrity of the sucker rod string that can lead to costly system failures. From an economic, operational and safety viewpoint, it is of prime importance to monitor the sucker rod for all types of alterations so that proper remedial action can be taken. More specifically, it is desirable to monitor sucker rod for alterations as the string is being removed from or inserted into the well borehole.

Electromagnetic Inspection (EMI) systems as well as eddy current surface inspection systems have been used to detect incised type flaws in sucker rod during manufacture and also during field use. Linear transducers have been used to measure sucker rod cross sectional dimensions, thereby providing a means of detecting wear type alteration of rod dimensions over extended lengths. These measurements have been limited to conventional sucker rod joints in the prior art. ICO Shearer (http:// www.icoshearerinc.com) offers an inspection service for continuous sucker rods. An inspection head assembly is used which will allow a 2 in. diameter rod which is pined and coupled to pass there through. This service is performed while the rod string is being removed from a well borehole. These prior art systems are, however, not practical for monitoring the condition of a conventional sucker rod string in "real-time" as it is pulled from or inserted into a well borehole.

Eddy current systems are very effective for at detecting surface defects such as cracks, grooves, gouges and the like. EMI systems have been used to detect localized defects or flaws in sucker rods. All of these systems require that a magnetic flux be induced within the rod. Surface defects result in magnetic flux leakage. Sensors measure the leakage and are thereby used to locate and even quantify the surface defect. An EMI system has been used to detect localized flaws in joints of tubulars, wherein the system employs Hall effect transducers and an energized coil that induces the magnetic flux within the tubular. Again, these measurements have been limited to inspecting the body of conventional sucker rod joints in the prior art, and are therefore are not practical for monitoring the condition of a conventional sucker rod string as it is pulled from or inserted into a well borehole. This limitation is partly due to forged pins at each end of a conventional sucker rod joint, and the non-consistent speed at which a rig crew pulls a conventional sucker rod string from a well borehole.

Several prior art systems are available for the inspection of continuous sections of wire rope. As examples, inspection systems wire rope inspection systems are disclosed in publications and several U.S. Patents to Noranda. An inspection system is offered by NDTech (http:///www.ndtettech.com/ndtbro.pdf). Prior art wire rope inspection systems are summarized in the publication "Inspection of Wire Ropes in Service: A Critical review", Frank A. Iddings and G. P. Singh, Materials Evaluation, Vol. 43, No. 13, pp. 1592–1605

(1985). The systems are typically portable, use permanent magnets to create a magnetic flux within the rope section being inspected, and all use the measure of magnetic flux leakage for flaw detection. Some systems measure the total magnetic flux to determine the effective cross-sectional area of the wire rope. This measurement is based upon the principle that for a saturated ferromagnetic rope, the magnetic flux is proportional to the cross-sectional area of the rope. A measure of magnetic flux can, therefore, be used to calculate the cross sectional area of the rope. Although not suitable for conventional sucker rod strings comprising joints, this technique can be adapted to measure the cross sectional area of continuous sucker rod strings, namely COROD strings, as the string is conveyed within a well borehole. It should be noted that a typical COROD string does not necessarily wear or abrade evenly over an extended length, thus the cross section can be oval or some shape other than round. In order to increase accuracy of cross sectional area measurements using linear systems on round rod, at least two measurements should be taken at ninety degrees and averaged. Computing cross sectional area from a measure of magnetic flux is, therefore, equivalent to, or even superior in accuracy to averaging multiple linear diameter measurements to calculate area.

Typically, all rod tests are related to operating stress levels such as yield stress, ultimate stress, and fatigue stress levels. Stress is defined as applied load divided by the cross sectional area of the rod. Cross sectional area, if measured directly with at least a 0.5% to 1.0% accuracy, is a much better indicator of rod condition that a cross sectional area computed from linear dimensions. If the rod is worn asymmetrically, cross sectional area computed from two linear dimensions taken at 90 degrees to each other will have significant error if the cross section is assumed to be circular. Prior art systems, including the Shearer system, measure rod dimensions using linear transducers. These dimensional measurements are subsequently used to compute cross sectional area of the rod which, as discussed above, can be in error if wear is oval.

Application for Canadian Patent No. 2,166,953 discloses apparatus and methods for measuring gross sectional area of wire rope by saturating a section of wire rope and subsequently determining the gross section from a measure of flux leakage. Furthermore apparatus and methods are disclosed for measuring geometry of flaws in wire rope using responses of Hall effect detectors. The reference does not teach the measurement of cross sectional area and flaws of continuous sucker rod, and does not teach the generation of real time reports of such measurements as a function of position along the continuous sucker rod.

SUMMARY OF THE INVENTION

The present invention is a system for measuring and recording dimensions and flaws in COROD as the sucker rod string is removed from or inserted into a borehole by means of a CORIG or other type of continuous rod handling injector.

COROD is passed through a sensor unit at the surface of the earth. The sensor unit is preferably attached to the CORIG, but can be located elsewhere as long as it is positioned between the head of the well and the service or transport reel receiving and coiling the COROD string. The sensor unit contains a magnet that saturates an increment of COROD within the sensor unit. The magnet is preferably a permanent magnet, but can alternately be an electromagnet. A coil within the sensor unit surrounds the COROD, and is used to measure magnetic flux induced within the COROD increment passing through the sensor unit. This measurement is used to compute cross sectional area of the COROD increment. One or more Hall effect transducers and sector coils are positioned within the sensor unit in the immediate vicinity of the COROD increment. Responses of the preferably multiple Hall effect transducers and sector coils are used to measure flux leakage. These measurements are, in turn, used to detect and to quantify localized flaws in the COROD such as grooves, gouges, pits and the like. It is again emphasized that the measurement is essentially continuous as the COROD string moves up and down within the sensor unit.

A depth measuring device cooperates with the COROD and CORIG or other type of continuous rod handling injector to determine the position of the increment of rod being measured with respect to a reference point, such as the downhole terminus of the COROD string. Magnetic flux measurements, Hall effect transducer and sector coils measurements, and depth measurements are input into a processor unit which contains a clock, an analyzer and a central processing unit (CPU). Magnetic flux is converted to cross sectional area of the COROD by means of the CPU using a predetermined calibration factor. Hall effect transducer and sector coils responses are combined with the clock output and depth measuring device response to obtain transducer responses as a function of position along the increment of rod being measured. These responses as a function of position are processed by an analyzer to determine (a) if a flaw is present, and (b) the type of flaw or flaw "geometry". Flaw geometry is determined from the "shape" of the transducer response as a function of position along the increment of rod being measured. The output from the depth measuring device is also input into the CPU. The CPU produces a tabulation or "log" of COROD cross sectional area, and a physical description or map of any COROD flaws as a function of position along the COROD string. This allows any mechanical COROD problems to be detected, located and quantified as the continuous sucker rod string is being conveyed within the well. Appropriate remedial actions can then be taken based upon the severity of the detected and quantified problem.

The system has a cross sectional area accuracy of about 0.5%. As an example, a round rod with a diameter of 1.000 in. which exhibits a measured 0.5% reduction in cross sectional area due to wear correspondingly exhibits a measurable 00025 in. reduction in diameter dimension. Vertical length measurements are made in increments of 0.25 in. with a location accuracy on the COROD string of about 12 in. This specification is significantly variably depending upon hardware and electronics of the system, and can be made more accurate if required. As an example, using a vertical length measuring wheel with a diameter of 11.853 in. and an encoder generating 2,048 encoder pulses per revolution of the measuring wheel, a linear measurement of 0.018 in. per encoder pulse is obtained. Combinations of wheel diameter and encoder sensitivity can be combined to obtain virtually any linear resolution required by a particular application of the system. Expectations are that flaws of about 0.015 in. wide or wider, and about 0.015 in. deep or deeper can be detected. Rod dimensions for round rod are computed from cross sectional area measurements.

The generated log typically indicates the time that each measured flaw is measured, the position and length dimensions of the flaw relative to the reference point on the COROD string, and the direction of rod movement when sampling occurs. The system also provides a real time calculated dimensional display of the COROD, and the current COROD cross sectional area as a function of length position.

The system is easily adapted to, installed on, and removed from existing CORIGS, can operate with COROD ranging in diameter from 0.750 in. to 1.25 in., and can operate at a CORIG gripper speeds of up to about 120 feet per minute.

Logged data is available at the well site in an Excel importable file, a hard copy graph, or an electronic file such as a disk. The system also has a visible, real time adjustable Go/No-Go limit indicator so that the GORIG can be immediately stopped if the sensed COROD condition fails to meet predetermined standards. The system is capable of operating at temperatures as low as −30 degrees Centigrade.

A DOS, Windows, Linux or other real time operating system based personal computer (PC) or industrial computer configured as a laptop system or a rack mounted system can be configured to serve as the system processor unit. The processor unit can be located as far away as 200 feet from the sensor unit, can be connected to the sensor unit by a wireless or hard wire link, and can be operated by a field rig crew.

BRIEF DESCRIPTION OF THE DRAWINGS

So that the manner in which the above recited features, advantages and objects the present invention are obtained and can be understood in detail, more particular description of the invention, briefly summarized above, may be had by reference to the embodiments thereof which are illustrated in the appended drawings.

DETAILED DESCRIPTION OF THE PREFERRED EMBODIMENT

The present invention is a system for measuring and recording physical properties of continuous sucker rod (COROD) as the COROD is removed from a borehole by means of a CORIG or other type of continuous rod handling injector. Alternately, physical properties can be measured as the COROD string is inserted into the borehole. This would be done only in extremely rare cases, as remedial repair of the rod string would require more time and incur more cost. The normal operation is to perform the inspection as the rod is being pulled from the borehole, prepare a report on the condition of the rod, and if necessary have a crew perform remedial work on the rod string.

Figure 1:
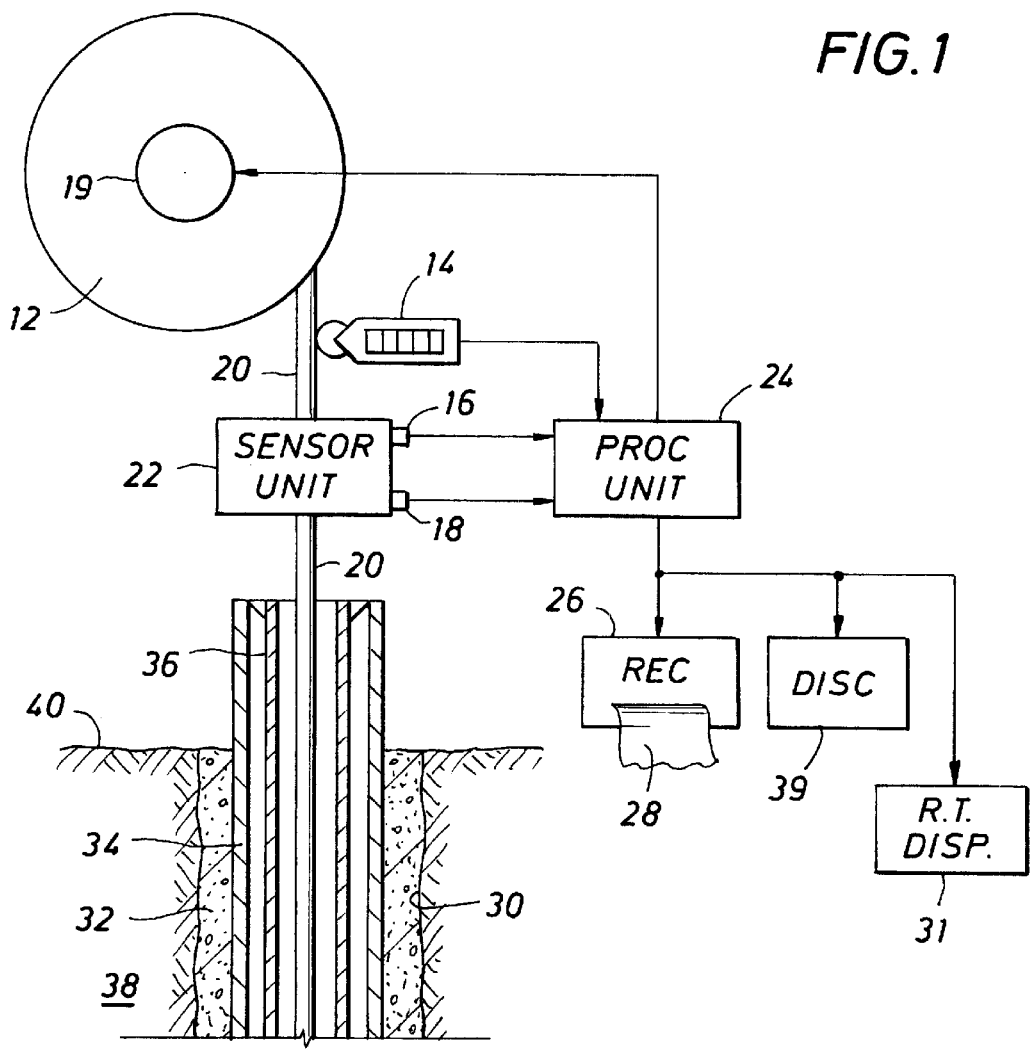
FIG. 1 is a highly conceptualized illustration of the invention that will be used to illustrate the basic components and operation principals of the invention.

FIG. 1 is a highly conceptualized illustration that will be used to illustrate the basic components and operation principals of the invention. A CORIG unit (or any other injection style pulling apparatus) 12 powered by a drive means 19 is used to convey a COROD string 20 within a well borehole 32 penetrating earth formation 38. The borehole 32 contains casing 34, which is surrounded by a cement sheath 32. The borehole also contains a tubing string 36 within which the COROD string 20 is positioned.

Still referring to FIG. 1, the COROD string 20 is passed through a sensor unit 22 at the surface of the earth 40. Although illustrated as a separate element for clarity, the sensor unit 22 is preferably attached to the CORIG unit 12. Alternately, the sensor package can be located anywhere between the head of the well and the CORIG unit 12 as long as it encompasses the COROD string 20. More specifically, the sensor head can be positioned between the well head and the injector, between the injector and a rod guiding element in the mast (not shown), or at the end of the guiding element prior to coiling the rod into a service or transport reel. A depth measuring device 14 is used in determining the length increment of COROD string 20 within the sensor unit 22 with respect to a reference point on the COROD string. As an example, the reference point can be the downhole end of the COROD string. Alternately, a clock (see FIG. 3) and a known speed of a gripper (not shown) on the CORIG can be used to determine the measured length increment. This alternate embodiment is conceptually feasible, but not preferred, since it is more accurate to measure the linear dimension distance rather than velocity of the rod, which typically does not move at a constants speed and which starts and stops frequently. Responses generated by the sensor unit 22 are direct to outputs 16 and 18. These outputs are operationally connected to a processing unit 24. The output of the depth measuring device 14 is also input to the processor unit 24. The processor unit 24 generates a record of cross sectional area and flaws in the COROD string 20, as will be discussed in detail in subsequent sections of this disclosure. Processor unit 24 is operationally connected through an output 27' to a recorder 26, which generates a hard copy 28 of COROD cross sectional area and flaws. The record is preferably a "log" of these data with respect to distance along the COROD string 20. The log of these data is preferably generated in real time and can be generated by means cooperating with the processor unit 24 by means of wireless communication. A real time hard copy presentation of the rod string is carried out on rare occasions. Typically, data are gathered and processed, and a report is produced to summarize the rod condition.

Processor unit output 27' can also be input into a data recording means 39 such as a magnetic disk, and into a real-time display unit 31 which presents an operator of the CORIG unit 12 with a "live" display of COROD condition as it is conveyed within the borehole 30. The processor unit 24 is also operationally connected to the drive means 19 of the CORIG 12. If COROD conditions, as determined by computations within the processor unit 24, exceed a predetermine standard, the processor unit can stop COROD conveyance within the borehole by disabling the drive unit 19. This step can alternately be performed manually by the CORIG operator based upon information from the real-time display 39. These features are technically feasible, but are not uses in normal operations. It is operationally desirable to remove the rod from the borehole as quickly as possible. The prime information is the condition of the rod and if the rod is in condition to be rerun into the well, as quickly as possible, thereby providing a preventative maintenance position for cost savings in the future. Specific operation information of prime importance is an indication of premature rod failure, or indication of the amount of salvageable rod which can be combined with new rod to form an operational rod string.

Figure 2:
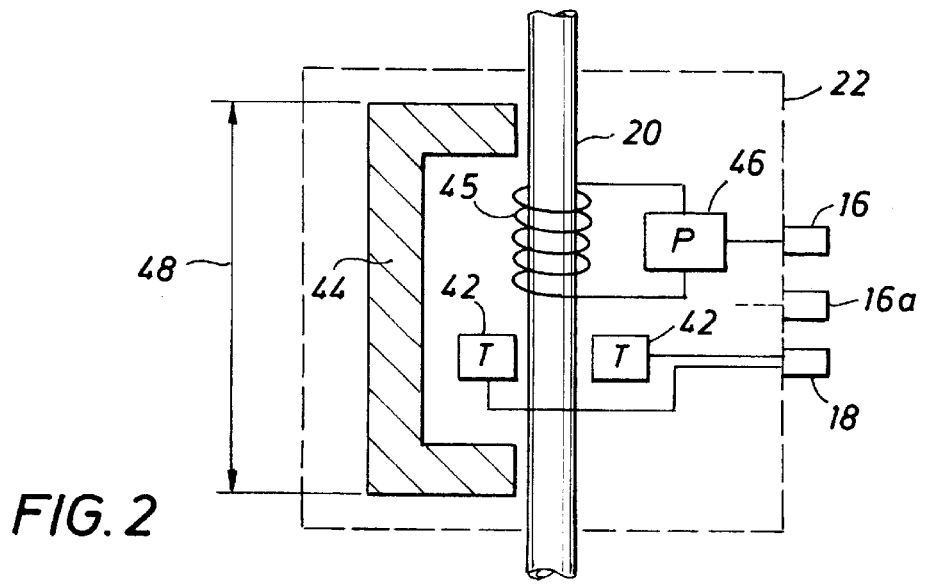
FIG. 2 is a conceptualized illustration of one of a possible plurality of sensor units used in the system.

Attention is directed to FIG. 2, which show conceptually the COROD string 20 passing through the sensor unit 22. The sensor unit 22 contains a magnet 44, which saturates an increment 48 of COROD. The magnet 44 is preferably a permanent magnet, but can alternately be an electromagnet. A coil 45 within the sensor unit 22 surrounds the COROD 20, and is used to measure magnetic flux induced within the increment 48 of COROD. This measurement is used to compute cross sectional area of the COROD. More specifically, if a ferromagnetic material such as the continuous sucker rod increment 48 is magnetically saturated by means of the magnet 44, the magnetic flux is proportional to the cross-sectional area of the rod increment. A measure the magnetic flux using the coil 45 can, therefore, be used to compute the cross sectional area of the COROD increment 48. Voltage induced by the magnetic flux sensed by the coin 45 is induced in the pickup 46 and output at 16. The output at 16 is proportional to the cross sectional area of the rod increment.

It is preferred to use a second pick up coil and associated pick up unit (not shown) which is electrically connected to an output 16' as illustrated conceptually by the broken line 17.

As discussed previously, a decrease in cross sectional area indicates rod wear. It is again noted that COROD does not necessarily wear or abrade evenly over an extended length, thus the cross section can be oval or some shape other than round. Computing cross sectional area from a measure of magnetic flux is, therefore, superior in accuracy to averaging multiple linear diameter measurements to calculate area. At a 1.0% accuracy in crass sectional measurement, the present system yields more accurate results for both round and elliptical rods than known prior art systems.

When a conductor is placed in a magnetic field with current flowing therein that is perpendicular to the magnetic field, a voltage that is induced perpendicular to both the current and the magnetic filed is known as the Hall voltage. Transducers based upon the Hall effect are available commercially. Because of the basic concept summarize above, Hall effect transducers are sensitive to geometry. Referring again to FIG. 2, one or more Hall effect transducers 42 are positioned in the immediate vicinity of the COROD 20. The number of transducers used is preferably a function of the nominal diameter of the COROD string. Responses of the preferably multiple Hall effect transducers and sectional coils are used to measure flux leakage. These measurements are, in turn, used to detect and to quantify localized flaws in the COROD such as groves, gouges, pits and the like. Furthermore, because of the sensitivity of Hall effect transducers to geometry, the shape of class of the flaw (e.g. grove, gouge, ring, pit, etc) can be determined from transducer responses. The Hall effect transducer responses are output from the sensor unit at 18.

Figure 3:
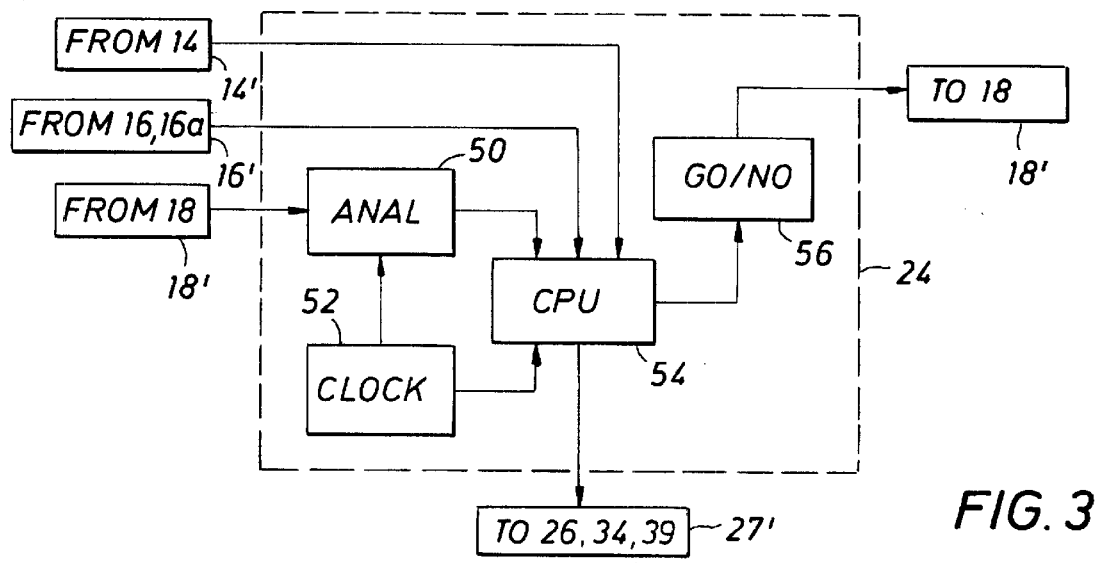
FIG. 3 is a conceptualized illustration of the processor unit of the system.

FIG. 3 is a conceptual illustration of the elements of the processor unit 24. Preferably two flux measurements from sensor unit output 16, and a second output 16a connected to a second identical unit (not shown but illustrated conceptually with a broken line 17), Hall effect transducer measurements from sensor unit output 18, and depth data from the depth measuring device 14 are input into the processor unit 24 at 16', 18', and 14', respectfully. For greater accuracy, four signals are presented to the processor 24. The processor unit 24 contains an analyzer element 50, which analyzes the shape of responses of the Hall effect transducers 42 as a function of position along the increment 48 being measured. This analysis yields quantitative information on the shape of the flaw such as groove, gouge, pit, ring and the like. Shape analysis of transducer response is known in the literature, and addressed by the previously referenced review article by Iddings and Singh. The processing unit also contains a clock 52 and a central processing unit (CPU) 54. Magnetic flux data input at 16' is converted to cross sectional area of the COROD increment 48 by means of the CPU 54 using a predetermined calibration factor. Hall effect transducer responses input at 18' are combined with the clock 52 output to obtain responses of the transducers 42 as a function of time, and combined with output from the depth measuring device 14 to obtain response as a function of position along the increment 48. These responses are processed by the analyzer 50 to determine (a) if flaws are present, (b) the geometry of the flaw as discussed previously, and (c) the cross sectional area. The CPU 54 processes and combines inputs from the analyzer 50, the clock 52, the input 16', and the input 14' to form an output at 54. The output is a record or "log" of COROD cross sectional area, and a physical description or map of any COROD flaws, tabulated as a function position along the COROD. Data are output to any or all devices including the recorder 26 which generates a hard copy 28, the magnetic recording means 39, and the real time display 31. This allows any mechanical COROD problems to be detected, located, quantified and recorded as the continuous sucker rod string 20 is being pulled from or inserted into the well borehole 30. Appropriate remedial actions can then be taken based upon the severity of the detected and quantified problem.

Still referring to FIG. 3, the processor unit 24 also contains a Go/No Go unit 56 which compares measured cross sectional area and flaws with predetermined standards to determine if the COROD increment meets operational and safety requirements. If the predetermined standards are not met, the Go/No Go unit can automatically terminate COROD conveyance within the well by disabling the drive unit 19. Alternately, the CORIG operator can monitor the real-time display 31 and manually disable the drive 19 if predetermined rod quality requirements are not met. n addition, an automated rod marking system (not shown) can be used to physically delineate rod sections that do not meet predetermined cross sectional area specifications.

Figure 4:
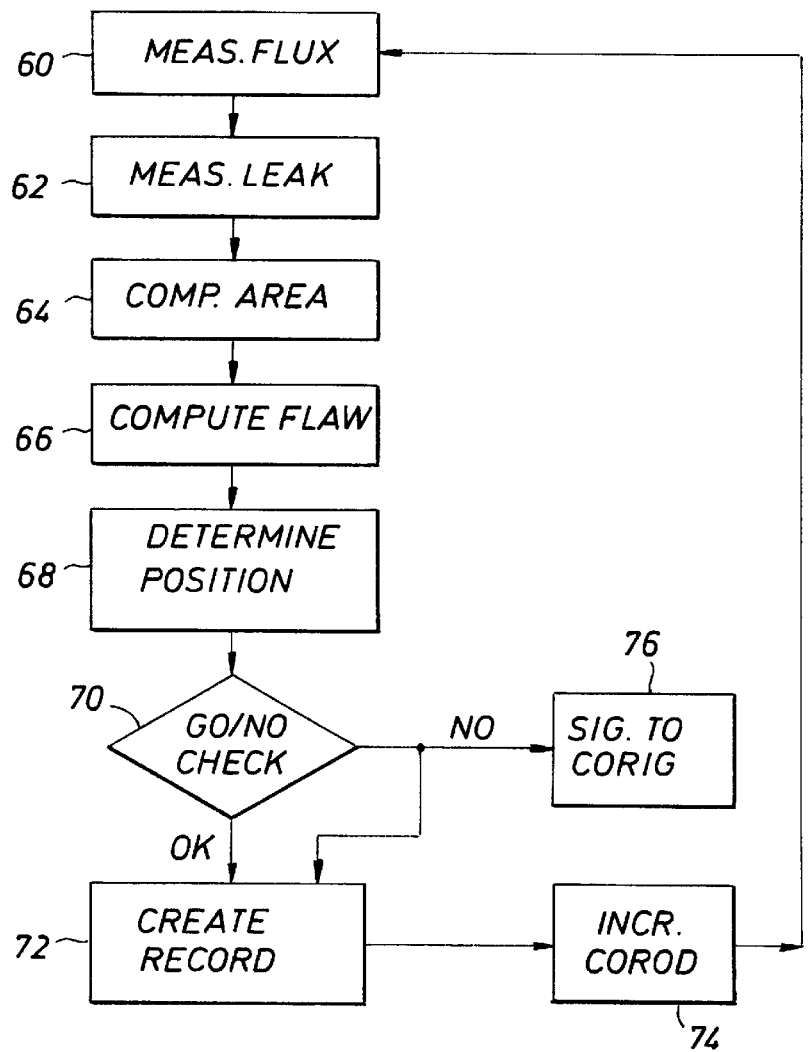
FIG. 4 is a flow chart of system operation.

FIG. 4 is a flow chart illustrating system operation. Flux is measured by the sensor unit at step 60, and magnetic leakage is measured by the sensor unit at step 62. Cross sectional area and flaw determination are obtained at steps 64 and 66, respectively, from the appropriate sensor unit measurements. The position of the increment being analyzed, with respect to a reference point on the COROD string, is obtained at step 68. A Go/No Go check is made at step 70. If measured physical properties of the increment 48 fails to meet predetermined specifications, a signal is sent to the CORIG unit drive 19 to terminate CORIG 12 operation. For reasons discussed previously, the closed loop rig control embodiment is feasible but not preferred. Alternately, an audible and visible system can operationally connected to the processor 24 to signal a rig operator of a flawed or reduced cross sectional section of rod. This would allow the operator to stop movement of the rod and to inspect the appropriate location. Since the rig operator typically does not have the ability or equipment to perform remedial work on the rod string, stopping and inspecting the rod may not be desirable from an operational rather than from a technical viewpoint.

Still referring to FIG. 4, a record of the measurement is also recorded at step 72. If predetermined conditions are met, a record of the measurement is made at step 72, and new increment 48 of COROD is positioned within the sensor unit at step 74. The sequence is then repeated for a new increment starting at step 60.

It should be understood that other equally effective sequences in data processing can be used, and the flow chart shown in FIG. 4 is shown to illustrate the basic operational concepts of the system in flow chart form.

The inspection system has a cross sectional area accuracy of about 0.5%. As an example, a round rod 20 with a diameter of 1.000 in. which exhibits a measured 0.5% reduction in cross sectional area due to wear correspondingly exhibits a measurable 00025 in. reduction in diameter dimension. Vertical length measurements 48 are made in increments of 0.25 in. with a location accuracy on the COROD string of about 12 in. This specification is significantly variably depending upon hardware and electronics of the system, and can be made more accurate if required. As an example, using a vertical length measuring wheel with a diameter of 11.853 in. and an encoder generating 2,048 encoder pulses per revolution of the measuring wheel, a linear measurement of 0.018 in. per encoder pulse is obtained. Combinations of wheel diameter and encoder sensitivity can be combined to obtain virtually any linear resolution required by a particular application of the system. Expectations are that flaws of about 0.015 in. wide or wider, and about 0.015 in. deep or deeper can be detected. Rod dimensions for round rod 20 are preferably computed in the CPU 50 from voltages induced in the coil 45.

The generated log (e.g. a hard copy record 28) typically indicates the time of each measured flaw, the position and length dimensions of the flaw relative to a reference point such as the downhole end of the COROD 20, and the direction of rod movement when sampling occurs. The system also provides a real-time two dimensional display of the COROD at 31, or alternately COROD cross sectional area as a function of length position along the string.

The system is easily adapted to, installed on, and removed from an existing CORIG 12, can operate with COROD 20 ranging in diameter from 0.750 in. to 1.25 in., and at a CORIG gripper speed of up to about 120 feet per minute.

Logged data are available at the well site as an Excel importable file, a hard copy graph 28, or an electronic file such as a disk 39. The previously discussed limit for the Go/No-Go 57 is visible and audible, and is optionally real time adjustable by the CORIG operator. The CORIG 12 can be immediately stopped if the sensed COROD condition fails to meet the predetermined standards. The system is capable of operating at temperatures as low as −30 degrees Centigrade.

A multilingual operating system personal computer (PC) laptop system or industrial system can be configured to serve as the system processor unit 24. The system processor 24 can be located as far away as 200 feet from the sensor unit 22, can be connected to the sensor unit 22 by a wireless or hard-wire link, and can be operated by a field rig crew.

While the foregoing disclosure is directed toward the preferred embodiments of the invention, the scope of the invention is defined by the claims, which follow.

What is claimed is:

1. A method for detecting a flaw in an increment of continuous sucker rod, comprising the steps of:
    (a) inducing a magnetic flux within said increment;
    (b) measuring magnetic flux leakage from said increment;
    (c) detecting said flaw from said measure of said magnetic leakage; and
    (d) generating a report describing geometry and location of said flaw along said continuous sucker rod, wherein the geometry described in the report comprises at least two dimensions.

2. The method of claim 1 wherein the geometry described in the report further comprises a third dimension.

3. The method of claim 2 comprising the additional steps of:
    (a) measuring said leakage as a function of position along said increment; and
    (b) determining geometry of said flaw from a shape of said measure of leakage as a function of position.

4. A method for determining cross sectional area of an increment of continuous sucker rod, comprising the steps of:
    (a) magnetically saturating said increment;
    (b) measuring magnetic flux within said increment;
    (c) determining said cross sectional area from said measure of said magnetic flux; and
    (d) generating a report defining a magnitude and position of said cross sectional area as a function of position along said continuous sucker rod.

5. A method for determining at least two physical properties of an increment of a continuous sucker rod string being conveyed within a borehole, comprising the steps of:
    (a) magnetically saturating said increment;
    (b) measuring magnetic flux within said increment;
    (c) measuring magnetic leakage from said increment;
    (d) determining at least one of said physical properties from said measure of magnetic flux;
    (e) determining at least one of said physical properties from said measure of magnetic leakage; and
    (f) generating a report describing at least one of said physical properties and a corresponding position along said increment, wherein at least one of said pysical properties is an at least two dimension geometry of a flaw along said continuous sucker rod.

6. The method of claim 5 comprising the additional step of determining in real-time a position of said increment with respect to a reference point on said continuous sucker rod string.

7. The method of claim 5 wherein said at least one of said physical properties obtained from said measure of magnetic flux is cross sectional area of said increment.

8. The method of claim 5 wherein said at least one of said physical properties from said measure of magnetic leakage is a flaw in said increment.

9. The method of claim 8 wherein said at least one of said physical properties from said measurement of magnetic leakage is geometry of said flaw, wherein said geometry is determined by:
    (a) measuring said leakage as a function of position along said increment; and
    (b) determining said geometry of said flaw from a shape of said measure of leakage as a function of position along said increment.

10. The method of claim 5 comprising the additional step of conveying said continuous sucker rod string within said borehole by means of a continuous sucker rod rig.

11. The method of claim 10 comprising the additional steps of:
    (a) comparing said at least two determined physical properties of said increment of a continuous sucker rod string with a predetermined set of values of said at least two physical properties; and
    (b) terminating operation of said rig based upon said comparison.

12. The method of claim 6 comprising the additional steps of recording said at least two measured physical properties as a function of distance at which measured from said reference point.

13. A system for measuring physical properties of an element of a continuous sucker rod string, comprising:
    (a) at least one sensor unit through which said string passes, wherein said sensor unit comprises (i) a magnet that saturates said element, said indication providing a geometric reprentation of the flaw in at least two dimension
(ii) a coil, and
(iii) at least one Hall effect transducer;
(b) a processor unit comprising a CPU which
(i) converts voltage induced within said coil by said saturated element into a measured cross sectional area of said element, and
(ii) converts magnetic leakage from said element and detected by said at least one Hall effect transducer into an indication of a measured flaw in said element; and
(c) means for generating a report of said measures of physical properties in real time.

14. The system of claim 13 further comprising means for measuring location of said element with respect to a reference point along said continuous sucker rod string.

15. The system of claim 14 further comprising means for recording said cross sectional area and said flaw as a function of distance along said continuous sucker rod string from said reference point.

16. The system of claim 15 further comprising:
(a) a rig for conveying said sucker rod string within a borehole;
(b) predetermined reference values stored within said processor unit for cross sectional area and flaws;
(c) means within said processor unit for comparing said reference values for cross sectional area and for flaws with said measured cross sectional area and said measured flaw; and
(d) means for terminating operation of said rig based upon said comparison.

17. The system of claim 15 wherein said means for recording comprises a recorder which produces a hard copy tabulating said cross sectional area and said flaw as a function of distance along said continuous sucker rod string from said reference point.

18. The system of claim 15 wherein said means for recording comprises a display unit which produces a real time display of said cross sectional area and said flaw as a function of distance along said coiled sucker rod string from said reference point.

19. The system of claim 15 wherein said means for recording comprises a magnetic disk for storing said cross sectional area and said flaw as a function of distance along said coiled sucker rod string from said reference point.

20. The system of claim 13 wherein said processing unit further comprises:
(a) means for measuring said leakage as a function of position along said element; and
(b) means for determining said geometry of said flaw from a shape of said measure of leakage as a function of position.

* * * * *